United States Patent
Rohner et al.

(10) Patent No.: US 10,197,334 B2
(45) Date of Patent: Feb. 5, 2019

(54) DENTAL FURNACE

(71) Applicant: Ivoclar Vivadent AG, Schaan (LI)

(72) Inventors: Gottfried Rohner, Altstätten (CH); Rudolf Jussel, Feldkirch-Gisingen (AT)

(73) Assignee: Ivoclar Vivadent AG, Schaan (LI)

( * ) Notice: Subject to any disclaimer, the term of this patent is extended or adjusted under 35 U.S.C. 154(b) by 19 days.

(21) Appl. No.: 15/293,673

(22) Filed: Oct. 14, 2016

(65) Prior Publication Data

US 2017/0030649 A1 Feb. 2, 2017

Related U.S. Application Data

(63) Continuation of application No. 13/093,167, filed on Apr. 25, 2011, now Pat. No. 9,492,253.

(30) Foreign Application Priority Data

Apr. 30, 2010 (EP) ..................... 10161640

(51) Int. Cl.
*F27D 5/00* (2006.01)
*A61C 13/20* (2006.01)
*F27B 17/02* (2006.01)

(52) U.S. Cl.
CPC ............ *F27D 5/0043* (2013.01); *A61C 13/20* (2013.01); *F27B 17/025* (2013.01)

(58) Field of Classification Search
CPC .............................. A61C 13/20; A61C 13/203
USPC .......... 432/120, 189, 205, 258, 253
See application file for complete search history.

(56) References Cited

U.S. PATENT DOCUMENTS

| | | | |
|---|---|---|---|
| 1,275,383 A | | 8/1918 | Campana |
| 1,336,762 A | * | 4/1920 | Swinnerton ........... F27D 5/0012 432/258 |
| 2,496,078 A | * | 1/1950 | Wentworth ........... B28B 7/0055 264/662 |
| 3,159,704 A | | 12/1964 | Marsteller |
| 4,139,341 A | | 2/1979 | Pfaffenbauer |
| 4,759,533 A | | 7/1988 | Sutor et al. |
| 4,996,969 A | * | 3/1991 | Dodgen ............... A47J 37/0704 126/25 A |
| 5,432,319 A | | 7/1995 | Indig |
| 5,788,485 A | | 8/1998 | Gruenenfelder et al. |
| 6,252,202 B1 | | 6/2001 | Zychek |
| 6,461,156 B2 | | 10/2002 | Kumazawa et al. |
| 2005/0006900 A1 | | 1/2005 | Lewis |
| 2005/0160544 A1 | * | 7/2005 | Geller ..................... A46B 9/02 15/160 |

(Continued)

FOREIGN PATENT DOCUMENTS

| | | |
|---|---|---|
| DE | 19905666 A1 | 8/1999 |
| JP | S56160380 A | 12/1981 |

(Continued)

*Primary Examiner* — Steven B McAllister
*Assistant Examiner* — Ko-Wei Lin
(74) *Attorney, Agent, or Firm* — Ann M. Knab; Thad McMurray

(57) ABSTRACT

In a dental furnace having a firing chamber (12) with a base and at least one receiving portion for dental restoration parts (40). The receiving portion has a plurality of support elements (26) that are arranged adjacent to one another and in particular have the same thickness, wherein said support elements (26) support the dental restoration part (40) during the firing process.

39 Claims, 5 Drawing Sheets

(56) References Cited

U.S. PATENT DOCUMENTS

| | | | |
|---|---|---|---|
| 2005/0229748 A1 | 10/2005 | Bleifuss et al. | |
| 2008/0199823 A1* | 8/2008 | Miller | F27B 17/025 432/258 |
| 2009/0090348 A1* | 4/2009 | Contarino, Jr. | A47J 37/074 126/25 R |
| 2009/0246739 A1 | 10/2009 | Jussel et al. | |
| 2010/0047731 A1 | 2/2010 | Zubler | |

FOREIGN PATENT DOCUMENTS

| | | | |
|---|---|---|---|
| JP | H09133473 A | 5/1997 | |
| JP | H11278946 A | 10/1999 | |
| JP | 2002226278 A | 8/2002 | |
| JP | 2005003897 A | 1/2005 | |
| JP | 2011079852 A | 4/2011 | |
| WO | WO 9119149 A1 * | 12/1991 | F27D 5/00 |

* cited by examiner

DENTAL FURNACE

CROSS-REFERENCE TO RELATED APPLICATIONS

This application is a continuation application and claims priority to U.S. application Ser. No. 13/093,167 filed on Apr. 25, 2011, which claims priority to European Patent Application No. 10 161 640.7, filed Apr. 30, 2010, all of which are hereby incorporated by reference in their entirety.

BACKGROUND OF INVENTION

The invention relates to a dental furnace, and more particularly to a dental furnace having an effective firing base.

DE 26 32 846 and U.S. Pat. No. 4,139,341, which is hereby incorporated by reference, disclose a dental furnace in which a hood-shaped firing chamber comprises a bottom that is configured as a base for the material being fired. The base for the material being fired is approximately arranged at the same level as the surrounding areas, thus substantially simplifying the handling.

Dental furnaces of this kind have stood the test of decades.

A similar dental furnace for example is known from DE 199 05 666 and U.S. Pat. No. 6,252,202 which is hereby incorporated by reference. This dental furnace also comprises a hood-shaped firing chamber that may be moved vertically relative to a firing platform. The firing platform is supported on an insulation plate and is designed to receive the dental restoration part by means of a recess.

For the burning of dental ceramics it is very important that a precise temperature profile is complied with during the burning or firing process. A temperature profile of this kind is ensured by controlled heating via one or more heating coils, wherein one temperature sensor or more temperature sensors are destined for controlling the interior temperature of the firing chamber. For financial reasons it is desirable to limit the number of temperature sensors, in particular in the case of vacuum dental firing furnaces as the passageways always must be sealed in a particular manner.

Typically, the dental restoration parts are centrally arranged in the firing chamber. Often, however, the insertion does not exactly take place in the center, or several dental restoration parts are burned or fired at the same time in order to considerably increase the efficiency of the firing process in this manner.

To ensure a given and uniform temperature in the firing furnace though, it is frequent practice to produce the receiving section for the dental restoration parts, e.g. the base for the material being fired, according to above-mentioned DE 26 32 846 with a good thermal conductivity and solid design, as it is also provided for example in the firing furnace according to DE 195 42 984 and U.S. Pat. No. 5,788,485, which is hereby incorporated by reference.

In order to shorten the firing cycle it has become known to accelerate the cooling down by means of opening the hood of the dental furnace. In this way, a temperature gradient is frequently generated in the receiving section, which may also result in the breakage of the receiving section.

SUMMARY OF THE INVENTION

The invention is based on the object of providing a dental furnace that is improved with regard to durability without impairing the exact implementation of the desired temperature profiles within the entire firing chamber.

This object is inventively solved by the independent claims. Advantageous further developments emerge from the subclaims.

According to the invention it is intended to provide the receiving section with a plurality of support elements that are arranged next to one another, for example in the form of a matrix. Surprisingly, the support elements do not break even in the case of being very thin, for example 3-5 mm, as long as the diameter of the support elements is significantly smaller than the diameter of the firing chamber, so that for example more than 10 support elements may cover the base of the firing chamber.

It is particularly favorable, if several support elements together form a support plane and in particular support the dental restoration part during the firing or burning process. The support elements are preferably arranged next to each other and have the same thickness in case of the same base level. If the base, however, is slightly concavely arched for example, it is also possible to use slightly thicker support elements in the middle and thinner support elements towards the outside. The top side of the support elements then practically ends on the same level so that a support plane for the dental restoration part is possible.

It is particularly preferred if the support elements have a good thermal conductivity. Surprisingly, this also ensures a uniform temperature within the firing chamber, as long as the firing furnace is not open. The support elements obviously well conduct the heat by means of the abutment against each other, and also the firing chamber base permits a homogenization or equalization of the temperature profile.

At the same time, the support elements protect the firing chamber base, and surprisingly tests did not at all exhibit any damages through cracks, even if the hood of the dental furnace had been opened, what is probably attributed to the lowering and thus to a better protection of the firing chamber base.

According to the invention it is particularly favorable that a multi-point support is provided for the restoration part. Eventual non-planar top sides of the dental restoration parts are compensated in this manner, and the inclination of the dental restoration part having a non-planar bottom side, to a slight tilting movement is considerably smaller, so that the danger of unwanted vibrations is also reduced.

A particularly favorable embodiment of the invention provides that the substantially disc-shaped support elements cover the firing chamber base as much as possible, that is to say they fill the entire area to the maximum. In the case of using round discs, it is to be understood that clearances remain, even if the discs are arranged in close package next each other.

If an entire coverage of the firing chamber base with round discs is desired, it is also possible to use a second layer of support elements that is arranged offset relative to the first layer on top thereof, so that the remaining gaps of the first layer are covered.

It is also possible to use any other shape of support elements instead of the round discs, for example triangle-shaped, hexagonal-shaped, square-shaped, non-square rectangular shaped or for example cross-shaped support elements.

In particular cross-shaped support elements may be arranged next to one another in a positive-locking manner so that they fill the firing chamber base in the area of the support base for the material to be fired without gaps and are connected in a positive-locking manner.

A particularly favorable embodiment provides that each support element comprises a substantially plane surface.

A particularly favorable embodiment provides that the support elements in the top view have a geometric form, wherein the geometric shapes of adjacent support elements are identical.

A particularly favorable embodiment provides that at least a portion of the surface of the support elements (26) comprises a structure for generating a multi-point, multi-line or multi-area support plane.

A particularly favorable embodiment provides that the support elements in the top view have the same geometric shape, and in particular fit together or mate with one another.

A particularly favorable embodiment provides that each support element has a width and/or a length that amounts to more than twice the height thereof, in particular approximately to five times the height thereof.

In a particularly favorable embodiment it is provided that the support elements are arranged on the base of the firing chamber of the dental furnace in close package, if applicable leaving slots and/or gaps and in particular leaving a margin or edge distance to the walls of the firing chamber.

In a particular favorable embodiment it is provided that support elements adjacent to one another at least partially abut against each other, and wherein outer support elements are arranged with a clearance or margin to the walls of the firing chamber of the dental furnace, said clearance or margin at least corresponding to the difference between the added up expansion path of the support elements upon heating from room temperature to a maximum of 1800° C, and the expansion path or movement of the base of the firing chamber upon heating from room temperature to a maximum of 1800° C.

In a particularly favorable embodiment it is provided that the support elements are disc-shaped and in particular at least partially are formed of $Al_2O_3$ and/or SiNi and/or Mullite and/or Cordierite and/or AlN and/or AlTi and/or SiC and/or $SiO_2$ and/or MgO and/or porcelain.

In a particularly favorable embodiment it is further provided that the support elements are arranged in a multiple arrangement of at least two support elements on the base of the dental furnace in a distributed manner.

In a particularly favorable embodiment it is provided that each support element has a point-symmetric shape such as a circle, a square, a hexagon, a cross or a star.

In a particularly favorable embodiment it is provided that at least one support element comprises a round shape or an outer contour that deviates from the circular shape.

In a particularly favorable embodiment it is provided that the support elements are formed in a disc-shaped manner from a solid and unfoamed material, in particular consist of ceramics whose softening temperature is higher than the maximum operating temperature of the dental furnace.

In a particularly favorable embodiment it is provided that at least two support elements engage positively one into the other.

In a particularly favorable embodiment it is provided that the receiving section comprises at least two layers of adjacent support elements, said layers being arranged one above the other.

In a particularly favorable embodiment it is provided that the support elements are of differing height, but at least end on same plane with respect to the top layer thereof in case several layers are arranged on top of each other.

In a particularly favorable embodiment it is provided that between the base of the dental furnace and the receiving section one at least one-piece disc having a high thermal conductivity is arranged.

In a particularly favorable embodiment it is provided that the disc is formed of SiC.

In a particularly favorable embodiment it is provided that the support elements substantially have a flat upper surface, if applicable slightly sloping towards their edges, and form a multi-point or multi-area support for dental restoration parts.

In a particularly favorable embodiment it is provided that the support elements are supported or applied on the firing chamber base that has a larger thermal conductivity than the heat insulating material of the dental furnace and in particular receives the support element in a positive-locking manner, said support elements in particular being formed of SiC.

In a particularly favorable embodiment it is provided that the support element for a dental furnace is characterized by the characterizing features of one of the preceding claims.

BRIEF DESCRIPTION OF THE FIGURES

Further advantages, details and features emerge from the following description of several exemplary embodiments of the invention in conjunction with the drawings, in which.

DETAILED DESCRIPTION

Figure 1:
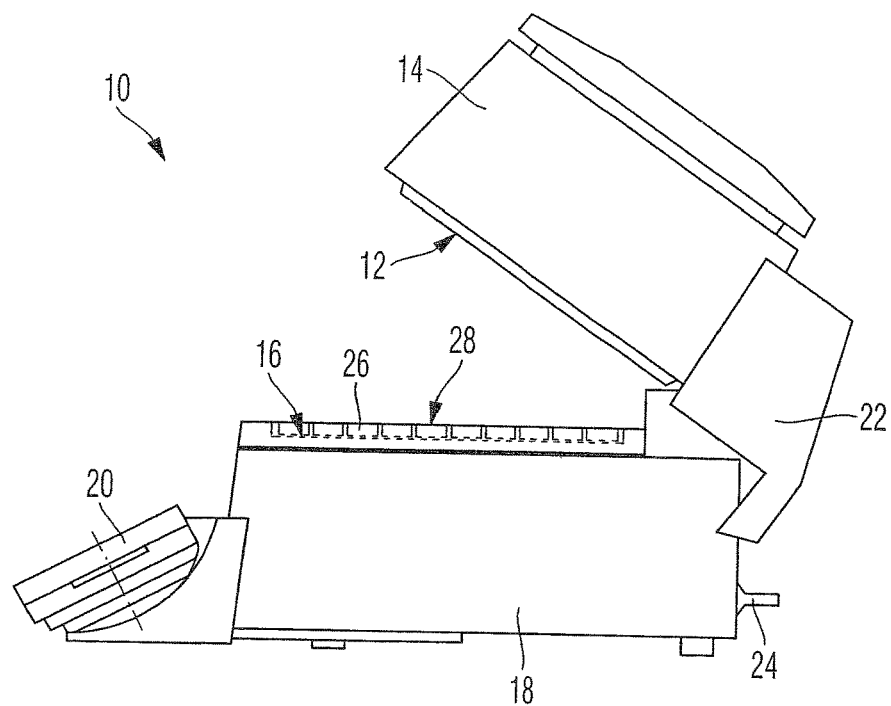
FIG. 1 illustrates a schematic view of an inventive dental furnace in one embodiment.

The dental furnace 10 of FIG. 1 comprises a firing chamber 12 that is formed with the aid of side walls and a top wall forming a hood 14. The base 16 of the firing chamber 12 is formed via a lower part 18 of the dental furnace 10. In a manner known per se, the dental furnace 10 comprises a control panel 20, and the lower part 18 and the hood-shaped upper part 14 are connected with one another via a hinge 22.

In the illustrated embodiment, the dental furnace 10 comprises a vacuum connection 24 via which the firing chamber 12 with closed hood may be subjected to a vacuum.

Figure 2:
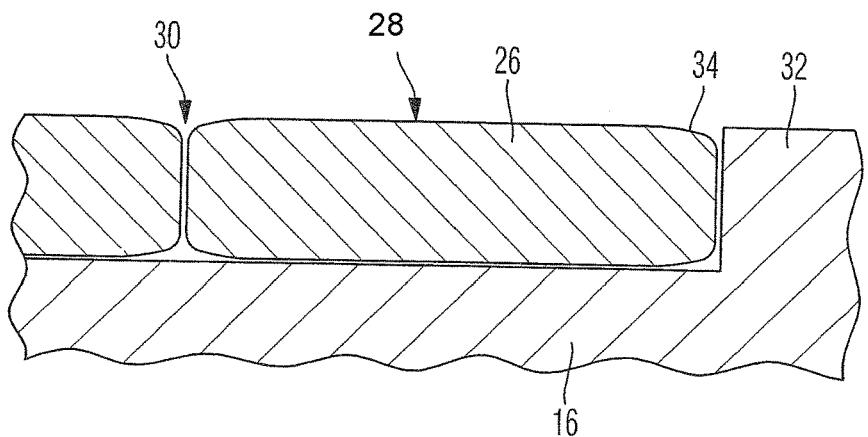
FIG. 2 illustrates an enlarged view of one detail of FIG. 1.

According to the invention, the firing chamber base 16 is a solid bottom covered by support elements 26, whose design becomes better apparent from FIG. 2. In this connection, the lower part 18 comprises a recess 28 in the area of the firing chamber base 16 and the height of the recess exactly corresponds to the height of a support element 26. The support elements 26 are shown disposed on and in contact with the solid bottom of chamber base 16.

From FIG. 2 it becomes apparent that the support elements 26 are formed and arranged so that they practically completely fill the recess 28. The support elements 26 may be formed in any suitable manner, however, they must be temperature-resistant up to a temperature that is clearly above the rated temperature of the firing furnace, e.g. 1600° C. They may entirely or partially consist of $Al_2O_3$. If the coefficient of thermal expansion of the firing chamber base 16 and the coefficient of thermal expansion of the support elements 26 differ from one another, this may be easily compensated by means of the clearance 30 between the support elements 26 and the edge 32 of the recess 28.

Figure 3:
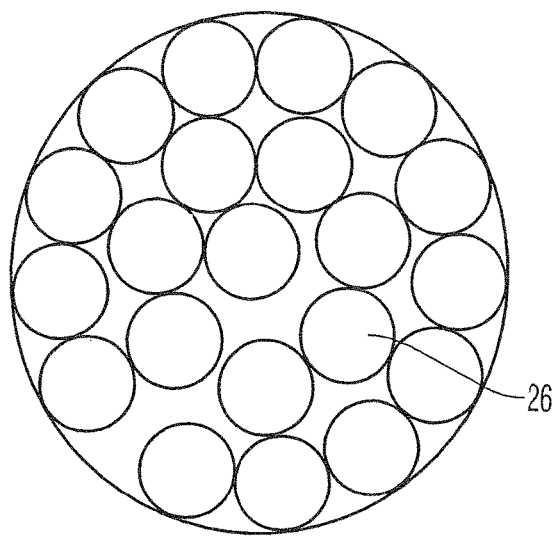
FIG. 3 illustrates a top view of one detail of a dental furnace according to the invention showing support elements and the firing chamber base.

It is to be understood that according to the invention the arrangement, number and shape of the support elements 26 may be adapted to the requirements in a wide range. The FIGS. 3 to 10 illustrate examples thereof. Thus, FIG. 3 shows circular, that is to say disc-shaped support elements 26 that may substantially be formed in a flat-cylindrical manner or that may comprise crowned roundings 34 at the edges thereof as shown in FIG. 2.

Figure 4:
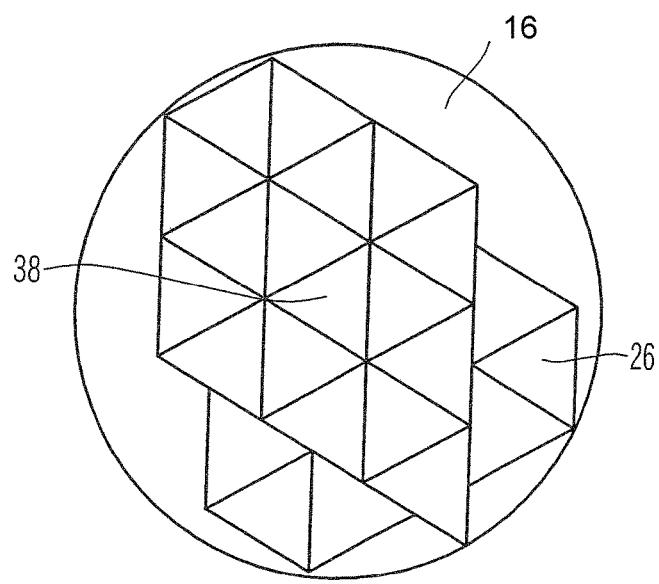
FIG. 4 illustrates a modified embodiment of a dental furnace according to the invention in the representation of FIG. 3.

FIG. 4 shows a multiple arrangement of triangle-shaped arrangements of support elements 26. In this embodiment it is favorable that primarily the central region 38 of the support element arrangement is covered in a gap-free manner, whereas at the edge area of the support element arrangement free spaces arise, that is to say the base 16 of the firing chamber is exposed at this position.

Figure 5:
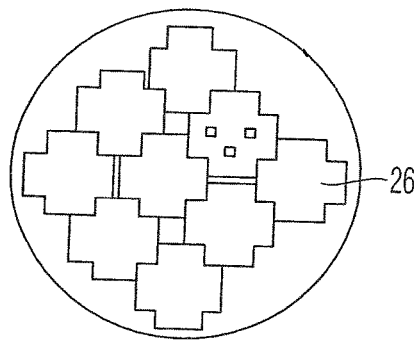
FIG. 5 illustrates a modified embodiment of a dental furnace according to the invention in the representation of FIG. 3.
Figure 6:
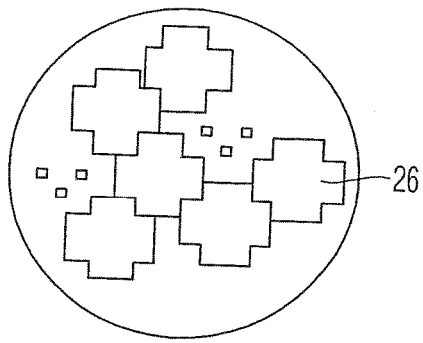
FIG. 6 illustrates a modified embodiment of a dental furnace according to the invention in the representation of FIG. 3.

FIG. 5 shows cross-shaped support elements 26 that may even be arranged in a still more unconstrained manner as shown in FIG. 6, but that are partially hooked into one another so that they may be together displaced or twisted.

Figure 7:
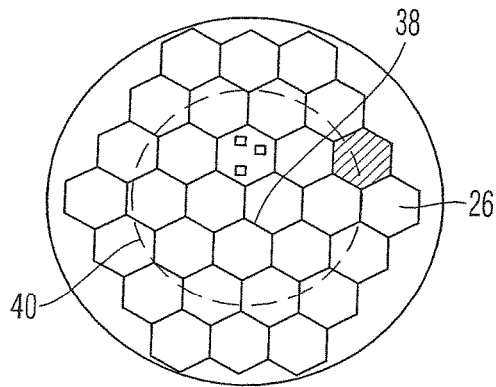
FIG. 7 illustrates a modified embodiment of a dental furnace according to the invention in the representation of FIG. 3.

FIG. 7 provides a hexagonal design of the support elements 26 that exposes considerable edge regions 38 of the firing chamber base 16, but fully covers the central area of the firing chamber base.

Figure 8:
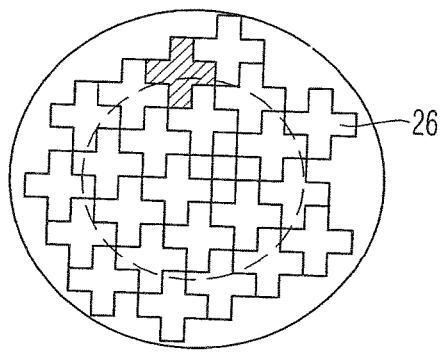
FIG. 8 illustrates a modified embodiment of a dental furnace according to the invention in the representation of FIG. 3.

FIG. 8 also illustrates cross-shaped support elements 26. These support elements have longer and thinner cross arms so that altogether, the result is a slimmer design of the cross if compared to the embodiment according to FIG. 5 and FIG. 6.

As can be seen in FIG. 7 and FIG. 8, the dental restoration parts 40 that are illustrated as a schematic circle in a dotted line, may be centrally arranged in the firing chamber. For example, the dental restoration part 40 may also be accommodated and supported in a plaster muffle or the like.

By means of the close interlocking, especially in the embodiments according to FIGS. 5 to 10, a good heat transfer between the disc-shaped support elements 26 is achieved, said heat transfer providing for the homogenization of the temperature within the firing chamber.

Figure 9:
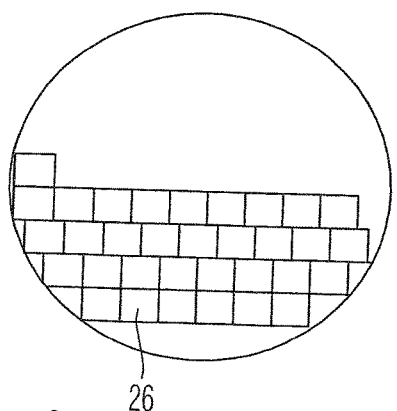
FIG. 9 illustrates a modified embodiment of a dental furnace according to the invention in the representation of FIG. 3.

FIG. 9 shows that the firing chamber base may also be covered partially, for example by square-shaped support elements 26.

Figure 10:
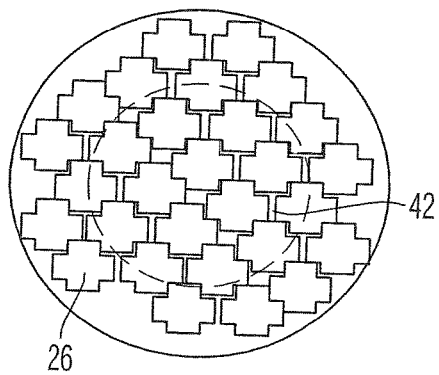
FIG. 10 illustrates a modified embodiment of a dental furnace according to the invention in the representation of FIG. 3.
Figure 11:
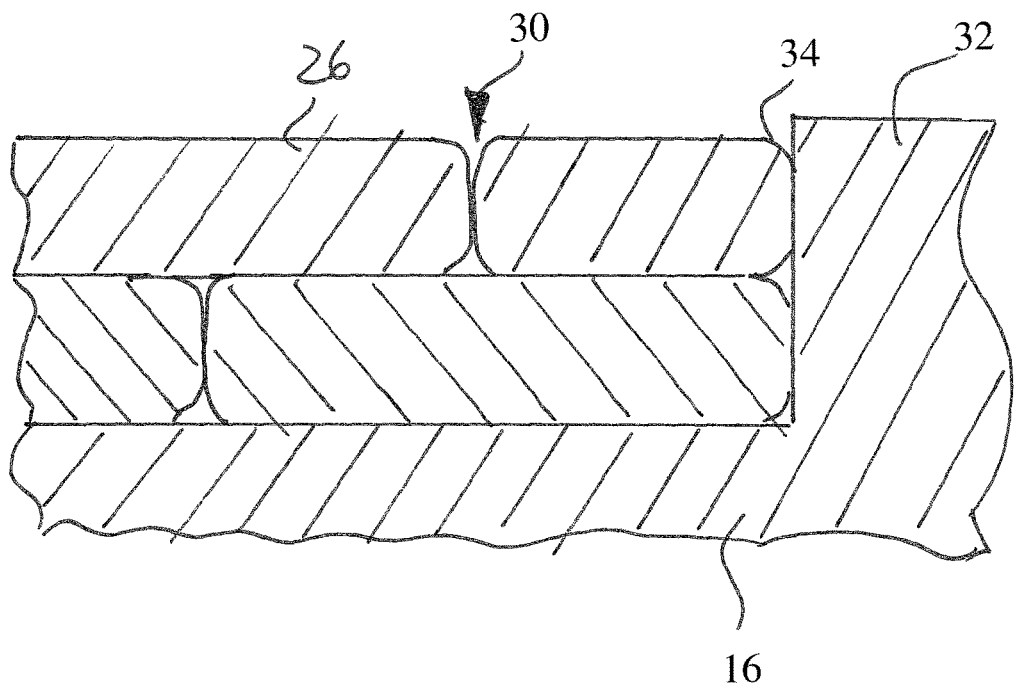
FIG. 11 illustrates a modified embodiment of a dental furnace according to the invention showing two layers of adjacent support elements.

A further embodiment of the inventive support elements is illustrated in FIG. 10. In this embodiment, cross-shaped support elements 26 are positively connected with one another leaving gaps 42.

Figure 12:
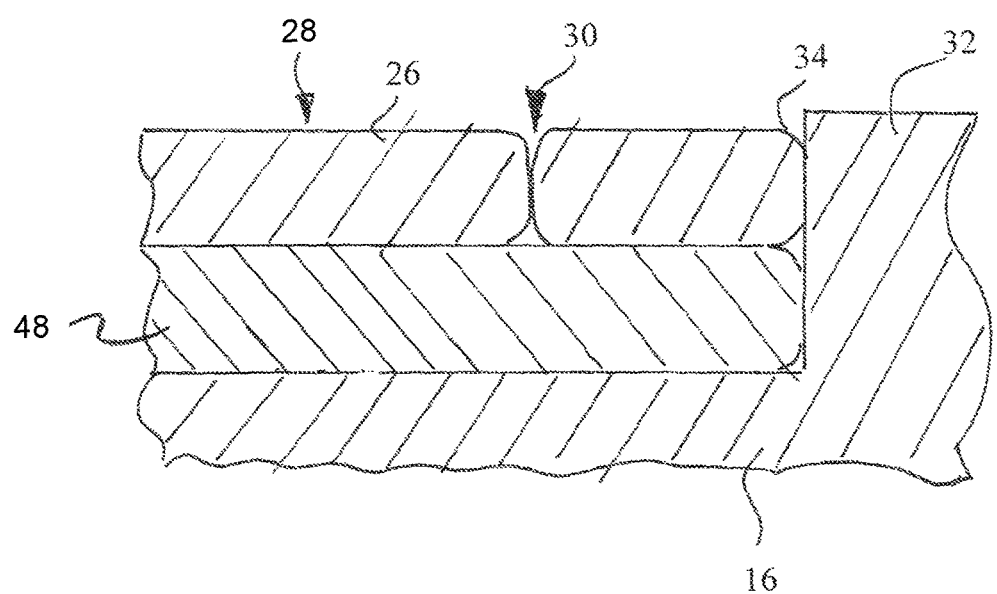
FIG. 12 illustrates a modified embodiment of a dental furnace according to the invention showing a one-piece disc arranged between the base of the dental furnace and the receiving section.

In FIG. 12, a one-piece disc 48 is arranged between the base 16 of the dental furnace and the support elements 26, which form a receiving section.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. A dental furnace comprising
a firing chamber comprising
side walls, a top wall and a stationary base having at least one receiving section for dental restoration parts, the receiving section having an open top,
wherein the at least one receiving section comprises a plurality of support elements disposed in close-packing arrangement to provide clearance between the support elements, wherein the clearance between the support elements corresponds to an amount of thermal expansion of the support elements upon heating from room temperature to a maximum of 1800° C., such that the support elements contact one another upon thermal expansion,
wherein the receiving section comprises a solid bottom, the plurality of support elements are disposed on and in contact with the solid bottom of the receiving section,
wherein at least some of said plurality of support elements form a common support plane for the dental restoration part,
wherein each support element comprises a substantially plane surface,
wherein the support elements are temperature-resistant at a temperature above 1600° C.

2. The dental furnace as claimed in claim 1, wherein at least a part of the surface of the support elements is provided with a structure for creating a multi-point, multi-line or multi-area support plane.

3. The dental furnace as claimed in claim 1, wherein said plurality of support elements in the top view have the same geometric shape, and mate with each other or fit together.

4. The dental furnace as claimed in claim 1, wherein each support element has a width, a length or both the width and length that amounts to more than twice its height.

5. The dental furnace as claimed in claim 1, wherein said plurality of support elements adjacent to one another at least partially abut against each other, and wherein elements of the support elements positioned near an outer edge of the receiving section are outer support elements, said outer support elements are arranged with a clearance or margin to the walls of the firing chamber of the dental furnace, said clearance or margin at least corresponding to the difference between the added up expansion path of said plurality of support elements upon heating from room temperature to a maximum of 1800° C., and the expansion path or movement of the base of the firing chamber upon heating from room temperature to a maximum of 1800° C.

6. The dental furnace as claimed in claim 1, wherein said plurality of support elements are formed in a disc-like manner and are at least partially formed of one of $Al_2O_3$, SiNi, Mullite, Cordierite, AlN, AlTi, SiC, $SiO_2$, MgO and porcelain.

7. The dental furnace as claimed in claim 1, wherein said plurality of support elements are arranged in a multiple arrangement consisting of at least two support elements on the base of the dental furnace.

8. The dental furnace as claimed in claim 1, wherein at least one support element comprises a round shape or an outer shape that deviates from the circular shape.

9. The dental furnace as claimed in claim 1, wherein the plurality of support elements are interlocking.

10. The dental furnace as claimed in claim 1, wherein the at least one receiving section at least comprises two layers of adjacent support elements, said layers being arranged one above the other.

11. The dental furnace as claimed in claim 1, wherein said plurality of support elements are differing in height, but at least end on the same plane with respect to a top layer thereof, in case several layers are arranged on top of each other.

12. The dental furnace as claimed in claim 1, wherein between the base of the dental furnace and the at least one receiving section at least one one-piece disc having a high thermal conductivity is arranged, said disc comprising SiC.

13. The dental furnace as claimed in claim 1, wherein said plurality of support elements have the same thickness.

14. The dental furnace as claimed in claim 4, wherein each support element has a width, a length, or both a width and length that amounts to up to approximately five times its height.

15. The dental furnace as claimed in claim 1, wherein said plurality of support elements are arranged in close packing on the base leaving a margin or edge distance to the walls of the firing chamber.

16. A support element for a dental furnace, characterized by the characterizing features of claim 1.

17. The dental furnace of claim 1, wherein the firing chamber ensures a uniform temperature when the furnace is closed.

18. The dental furnace as claimed in claim 10, wherein the two layers are offset relative to each other such that gaps of one layer are covered.

19. The dental furnace as claimed in claim 1, wherein said plurality of support elements are round, triangle-shaped, hexagonal-shaped, square-shaped, non-square rectangular shaped or cross-shaped.

20. The dental furnace as claimed in claim 1, wherein said plurality of support elements are arranged next to one another in a positive-locking manner.

21. The dental furnace as claimed in claim 1, wherein said plurality of support elements comprise a substantially planar surface.

22. A dental furnace comprising
a firing chamber, wherein the firing chamber comprises side walls, a top wall and a stationary base having at least one receiving section for dental restoration parts,
wherein the at least one receiving section comprises a plurality of support elements disposed in close-packing arrangement to provide clearance between the support elements, wherein the clearance between the support elements corresponds to an amount of thermal expansion of the support elements upon heating from room temperature to a maximum of 1800° C., such that the support elements contact one another upon thermal expansion,
wherein at least some of said support elements form a common support plane for the dental restoration part,
wherein each support element comprises a substantially plane surface, and
wherein the receiving section comprises a solid bottom, the plurality of support elements are disposed on and in contact with the solid bottom of the receiving section,
wherein a width, a length, or both the width and length of each support element is greater than a height thereof,
wherein the support elements are temperature-resistant at a temperature above 1600° C.

23. The dental furnace as claimed in claim 22, wherein at least a part of the surface of the support elements is provided with a structure for creating a multi-point, multi-line or multi-area support plane.

24. The dental furnace as claimed in claim 22, wherein said plurality of support elements in the top view have the same geometric shape, and mate with each other or fit together.

25. The dental furnace as claimed in claim 22, wherein the width, length, or both the width and length amounts to more than twice the height.

26. The dental furnace as claimed in claim 22, wherein said plurality of support elements are arranged in close packing on the base of the firing chamber of the dental furnace, leaving slots and/or gaps.

27. The dental furnace as claimed in claim 22, wherein said plurality of support elements adjacent to one another at least partially abut against each other, and wherein elements of the support elements positioned near an outer edge of the receiving section are outer support elements, said outer support elements are arranged with a clearance or margin to the walls of the firing chamber of the dental furnace, said clearance or margin at least corresponding to the difference between the added up expansion path of said plurality of support elements upon heating from room temperature to a maximum of 1800° C., and the expansion path or movement of the base of the firing chamber upon heating from room temperature to a maximum of 1800° C.

28. The dental furnace as claimed in claim 22, wherein said plurality of support elements are formed in a disc-like manner and are at least partially formed of one or more of $Al_2O_3$, SiNi, Mullite, Cordierite, AlN, AlTi, SiC, $SiO_2$, MgO and porcelain.

29. The dental furnace as claimed in claim 22, wherein said plurality of support elements are arranged in a multiple arrangement consisting of at least two support elements on the base of the dental furnace.

30. The dental furnace as claimed in claim 22, wherein at least one support element comprises a round shape or an outer shape that deviates from the circular shape.

31. The dental furnace as claimed in claim 22, wherein said plurality of support elements are interlocking.

32. The dental furnace as claimed in claim 22, wherein the at least one receiving section at least comprises two layers of adjacent support elements, said layers being arranged one above the other.

33. The dental furnace as claimed in claim 22, wherein said plurality of support elements are differing in height, but at least end on the same plane with respect to a top layer thereof, in case several layers are arranged on top of each other.

34. The dental furnace as claimed in claim 22, wherein between the base of the dental furnace and the at least one receiving section, at least one one-piece disc having a high thermal conductivity is arranged, said disc comprising SiC.

35. The dental furnace as claimed in claim 22, wherein said plurality of support elements have the same thickness.

36. The dental furnace as claimed in claim 26, wherein the width, length, or both the width and length amounts to up to approximately five times its height.

37. The dental furnace as claimed in claim 27, wherein said plurality of support elements are arranged in close packing on the base leaving a margin or edge distance to the walls of the firing chamber.

38. A support element for a dental furnace, characterized by the characterizing features of claim 22.

39. A dental furnace comprising
- a firing chamber comprising
    - side walls, a top wall and a stationary base having at least one receiving section for dental restoration parts, the receiving section having an open top,
    - wherein the at least one receiving section comprises a plurality of support elements, wherein no gap exists between adjacent support elements,
    - wherein the receiving section comprises a solid bottom, the plurality of support elements are disposed on and in contact with the solid bottom of the receiving section,
    - wherein at least some of said plurality of support elements form a common support plane for the dental restoration part,
    - wherein each support element comprises a substantially plane surface,
    - wherein the support elements are temperature-resistant at a temperature above 1600° C.

* * * * *